(12) United States Patent
Liu

(10) Patent No.: US 6,200,294 B1
(45) Date of Patent: Mar. 13, 2001

(54) MULTIFUNCTIONAL SYRINGE WITH SAFETY SLIDE SLEEVE

(76) Inventor: Wen-Neng Liu, 19508 Nicholas Ave., Cerritos LA, CA (US) 90701

( * ) Notice: Subject to any disclaimer, the term of this patent is extended or adjusted under 35 U.S.C. 154(b) by 0 days.

(21) Appl. No.: 09/228,288

(22) Filed: Jan. 11, 1999

Related U.S. Application Data

(63) Continuation-in-part of application No. 08/916,929, filed on Aug. 22, 1997.

(51) Int. Cl.[7] .................................................. A61M 5/32
(52) U.S. Cl. ............................ 604/198; 604/171; 604/535
(58) Field of Search ..................................... 604/174, 177, 604/171, 162, 158, 164.01, 164.08, 165.01–165.02, 110, 198, 195, 197, 263, 192, 905, 283, 256, 175, 533–536; 128/919

(56) References Cited

U.S. PATENT DOCUMENTS

| | | | |
|---|---|---|---|
| 4,676,783 | * | 6/1987 | Jagger et al. . |
| 5,259,843 | * | 11/1993 | Watnabe et al. . |
| 5,382,240 | * | 1/1995 | Lam . |
| 5,800,400 | * | 9/1998 | Hogan . |
| 5,928,199 | * | 7/1999 | Makadami . |

* cited by examiner

Primary Examiner—Richard K. Seidel
Assistant Examiner—LoAn H. Thanh
(74) Attorney, Agent, or Firm—Rosenberg, Klein & Lee

(57) ABSTRACT

A multifunctional syringe with safety slide sleeve, including: a connecting tube, a top end of the connecting tube being formed with a needle connecting section for connecting with an injection needle, a bottom end of the connecting tube being connected with an infusion tube, an outer circumference of the connecting tube being formed with a latching groove near the top end thereof, at least one guiding rib being formed on the connecting tube and axially downward extending from a lower side of the latching groove, the guiding rib being downward tapered; and a safety slide sleeve slidably fitted around the infusion tube or the connecting tube, a bottom end of a fitting hole of the slide sleeve being formed with an inward extending latching flange. When the slide sleeve is slided upward, the latching flange is guided by the guiding rib to be smoothly latched in the latching groove of the connecting tube. Accordingly, the injection needle can be totally received and hidden in the slide sleeve so as to avoid impalement or infection of other people with AIDS, hepatitis, etc.

5 Claims, 6 Drawing Sheets

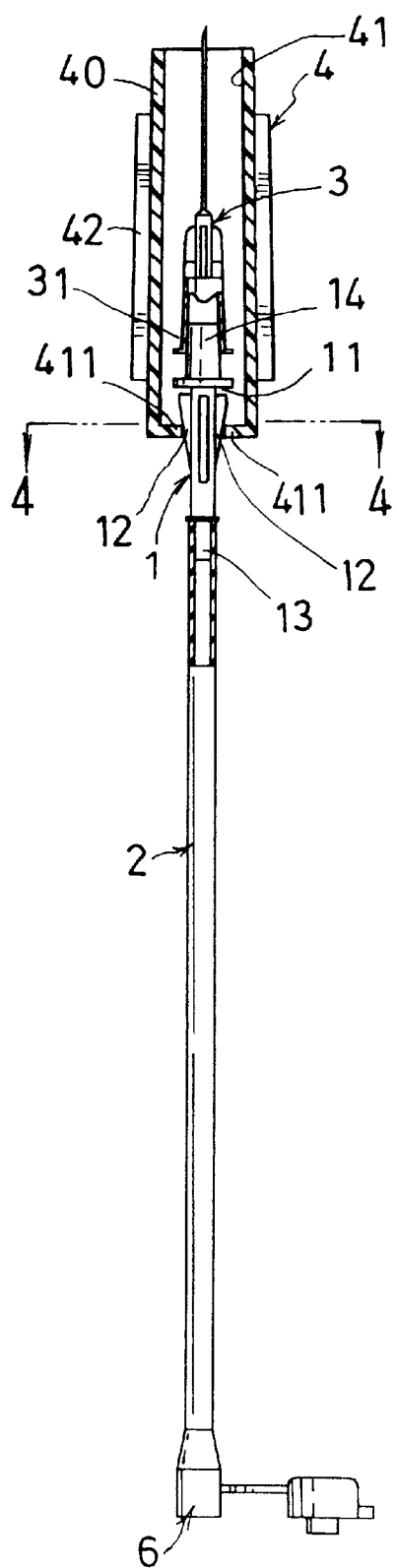
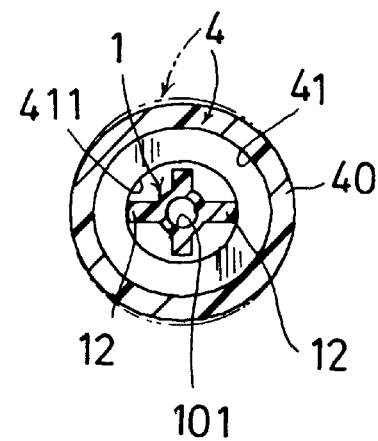
FIG. 4
FIG. 3

MULTIFUNCTIONAL SYRINGE WITH SAFETY SLIDE SLEEVE

CROSS-REFERENCE TO RELATED APPLICATION

This application is a Continuation-in-Part of U.S. patent application Ser. No. 08/916,929, entitled "An Multifunctional Safety Infusion Set With Injection Needle Retractable In A Wing-Equipped Sheath", filed on Aug. 22, 1997, now pending.

BACKGROUND OF THE INVENTION

1. Field of the Invention

The present invention relates to a multifunctional syringe with safety slide sleeve, and more particularly to a syringe in which after injection, the injection needle is retracted and hidden in a safety slide sleeve so as to avoid impalement and infection of medical personnel or other people.

2. Description of the Prior Art

All the existing medically used I.V. fustula set, scalp vein set and general infusion injection needle include a single injection needle serially connected with an infusion tube for intravenous injection. A needle sheath is fitted around the injection needle. In injection, the needle sheath is removed from the injection needle. After the injection is completed, the needle sheath is again fitted around the injection needle for avoiding impalement. However, the needle sheath has a very small fitting hole. Therefore, it often takes place that when inserting the injection needle back into the needle sheath, medical personnel are incautiously impaled by the used injection needle. This may lead to infection of the medical personnel with AIDS virus, hepatitis, etc.

In addition, in the medical dropper equipments such as I.V. fustula set, scalp vein set, general infusion injection needle and intravenous infusion needle, a wing-type fixing plate structure is provided. However, such wing-type fixing plate cannot be replaceably applied to different kinds and sizes of needles so that the medical institute must prepare all the above needles for multiple uses. This leads to inconvenience in use.

SUMMARY OF THE INVENTION

It is therefore a primary object of the present invention to provide a multifunctional syringe with safety slide sleeve which slidably firmly engages with an upper end of a connecting tube so as to retract and hide the injection needle connected with the top of the connecting tube in the safety slide sleeve. Accordingly, after injection, the injection needle is totally hidden in the slide sleeve and then discarded. Therefore, the injection needle is prevented from being exposed outside so as to avoid impalement or infection of other people. Moreover, the present invention has simple structure and is applicable to scalp vein set, intravenous infusion needle and general dropper infusion set so as to avoid waste of medical resource.

The present invention can be best understood through the following description and accompanying drawings, wherein:

BRIEF DESCRIPTION OF THE DRAWINGS

FIG. 3 is a sectional view of the present invention, in which after injection, the slide sleeve is pushed upward;

FIG. 4 is a sectional view taken along line 4-4 of FIG. 3;

DETAILED DESCRIPTION OF THE PREFERRED EMBODIMENTS

Figure 1:
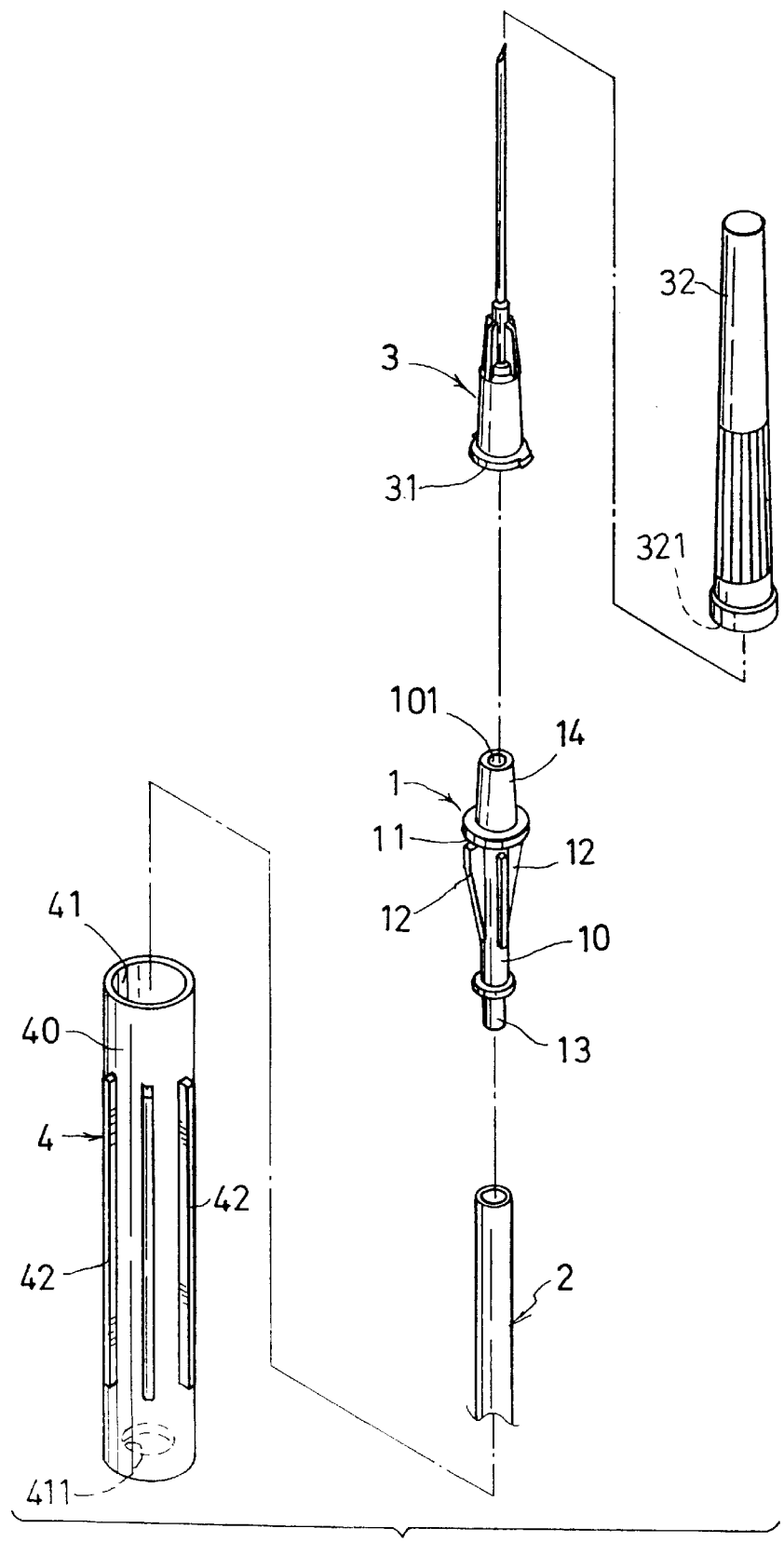
FIG. 1 is a perspective exploded view of the present invention.

Please refer to FIGS. 1 to 5. The multifunctional syringe of the present invention includes: a connecting tube 1, an outer circumference of the connecting tube 1 being formed with a latching groove 11, at least one guiding rib 12 being disposed on the connecting tube 1 under the latching groove 11; an infusion tube 2 serially connected to a bottom end of the connecting tube 1; an injection needle 3 serially connected with a top end of the connecting tube 1, in normal state, the injection needle 3 being fitted in a protective cavity 321 of a needle sheath 32; and a safety slide sleeve 4 slidably fitted around the infusion tube 2 or the connecting tube 1. A bottom end of a fitting hole 41 of the slide sleeve 4 is formed with an inward extending latching flange 411. When the slide sleeve 4 is slided upward, the latching flange 411 is guided by the guiding rib 12 to smoothly latch with the latching groove 11 of the connecting tube 1. Accordingly, the injection needle 3 can be totally received and hidden in the slide sleeve 4 so as to avoid impalement or infection of other people.

The connecting tube 1 includes: a tube body 10 formed with a central axial through hole 101 as a passage of liquid medicine; a latching groove 11 formed on outer circumference of the tube body 10 near the top end thereof for latching with the latching flange 411 of the slide sleeve 4; at least one guiding rib 12 axially downward extending from a lower side of the latching groove 11 of the tube body 10, the guiding rib 12 being downward tapered; an infusion tube connecting section 13 formed at lower end of the tube body 10 for connecting with the infusion tube 2; and a needle connecting section 14 formed at top end of the tube body 10 for snugly fitted with a needle holder 31 disposed at bottom end of the injection needle 3.

The safety slide sleeve 4 includes: a sleeve section 40 formed with a central axial fitting hole 41 in which the connecting tube 1 or the infusion tube 2 is fitted, the bottom end of the fitting hole 41 being formed with an inward extending latching flange 411 for slidably latching with the latching groove 11 of the connecting tube 1; and multiple slipproof ribs 42 axially formed on outer circumference of the sleeve section 40 for facilitating holding of the slide sleeve 4.

Different types of injection needles are replaceably connected with the connecting tube 1 as necessary for use in I.V. fustula set, scalp vein set, dropper infusion needle, etc.

Figure 2:
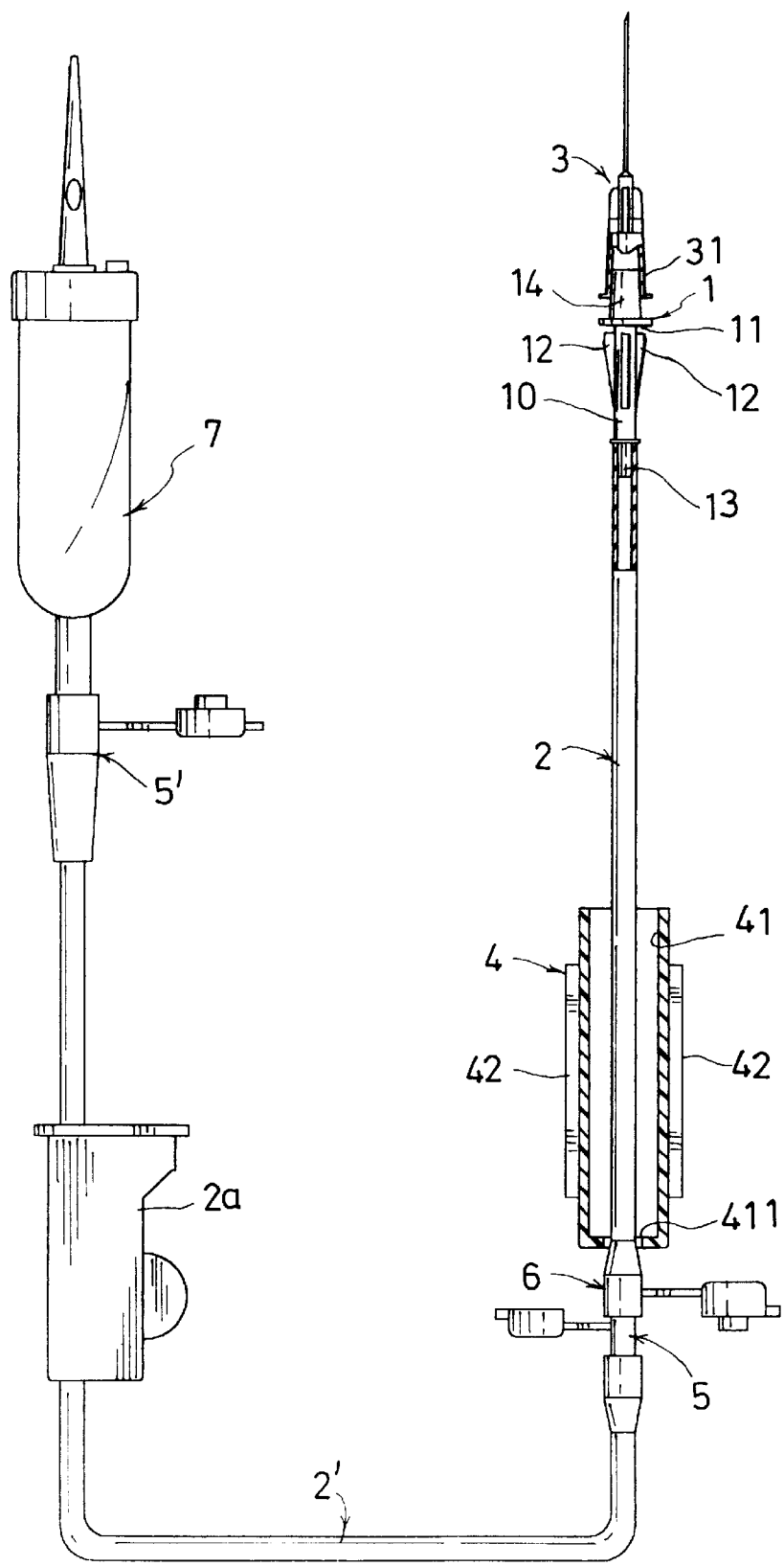
FIG. 2 is a sectional view of the present invention in injection.
Figure 5:
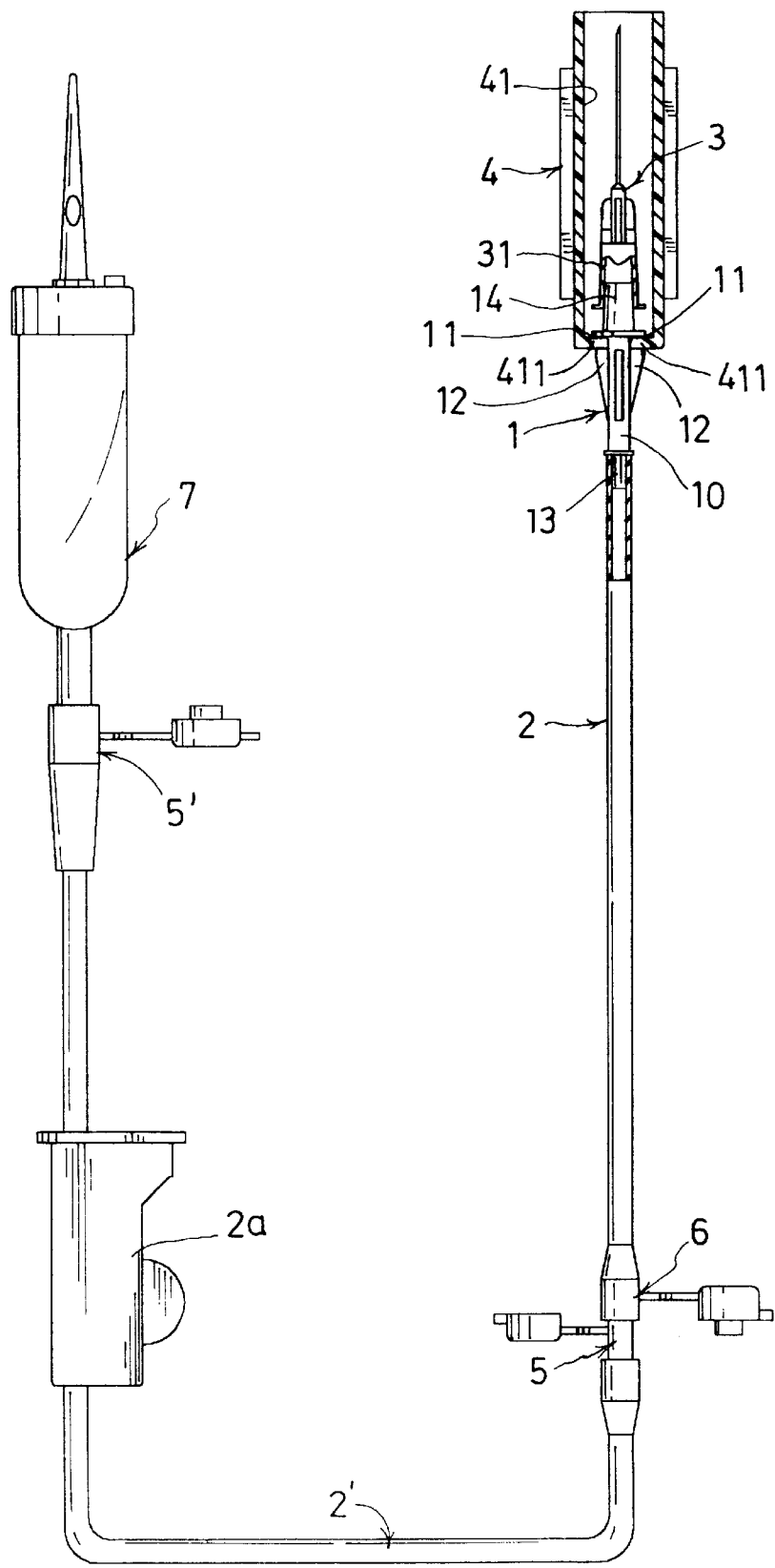
FIG. 5 is a sectional view of the present invention, showing that the injection needle is hidden in the slide sleeve.

Referring to FIG. 2, in application, a connector 6 of the infusion tube 2 is serially connected an output connector 5 of a dropper infusion throttle tube 2'. The needle connecting section 14 of the top end of the connecting tube 1 is connected with the needle holder 31 of the injection needle 3. An input connector 5' of the dropper infusion throttle tube 2' is serially connected with a dropper connector 7 to form a dropper infusion needle. After injection, the medical personnel can hold the slide sleeve 4 with one hand and slide the slide sleeve 4 upward as shown in FIGS. 3 and 4. When the latching flange 411 of the bottom end of the slide sleeve 4 is slided over the guiding rib 12, the guiding rib 12 outward expands the latching flange 411 so as to slightly resiliently expand and deform the bottom end of the slide sleeve 4 from an original circular shape into a substantially elliptic shape as shown by phantom line of FIG. 4. Accordingly, the latching flange 411 of the slide sleeve 4 can smoothly pass through the guiding rib 12 to latch with the latching groove 11 of the connecting tube 1. Under such circumstance, the injection needle 3 is totally enclosed in the slide sleeve 4 to avoid impalement of other people as shown in FIG. 5.

Alternatively, in the syringe of the present invention, a throttle 2a can be installed on the infusion tube 2 to directly form a dropper infusion throttle tube not shown).

Figure 7:
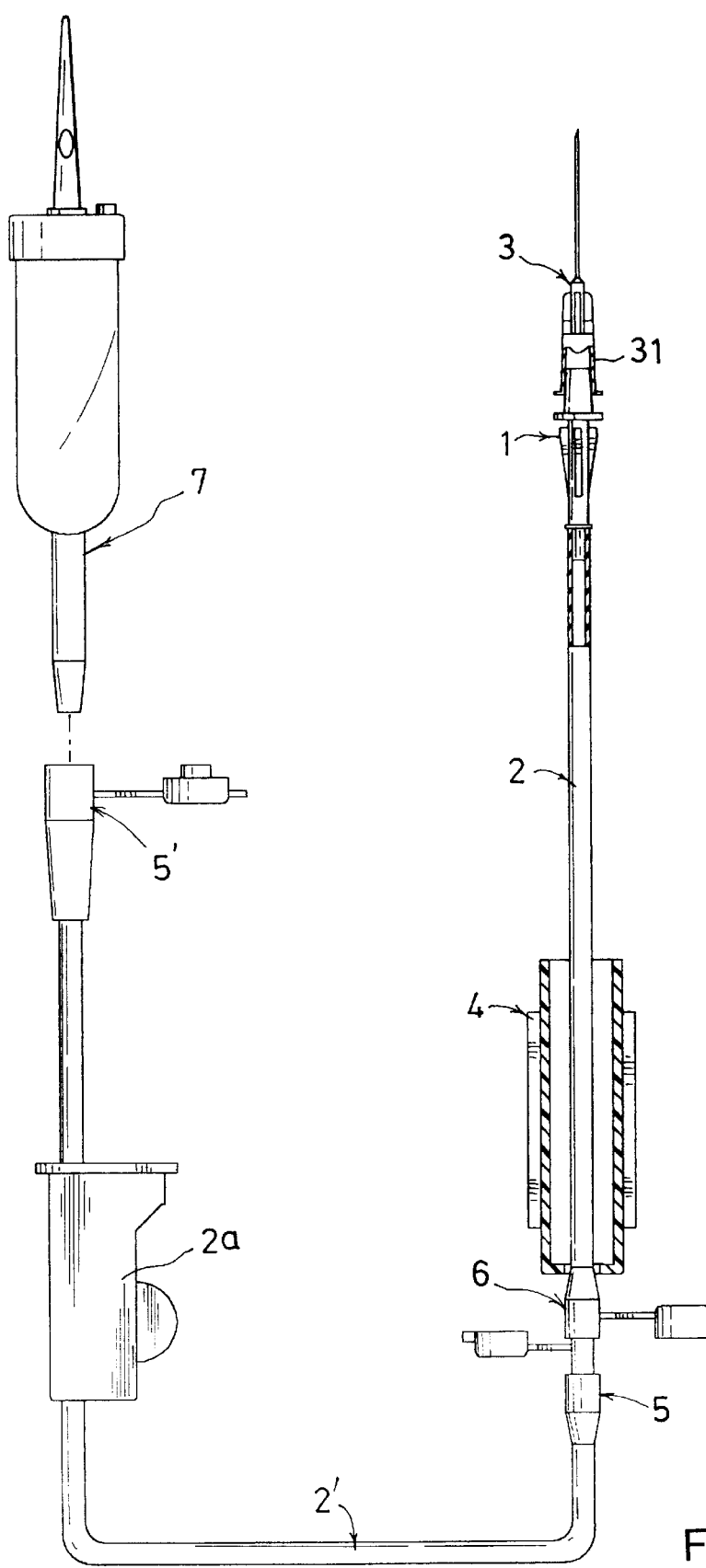
FIG. 7 shows that the dropper infusion throttle tube is separated from the dropper connector of the present invention.

Referring to FIG. 7, the input connector 5' of the input end of the dropper infusion throttle tube 2' is connected with the dropper connector 7. According to actual requirement of the medical side, multiple infusion tubes (not shown) can be serially connected between the dropper connector 7 and the input connector 5' so as to elongate the infusion distance. (The existing dropper infusion throttle tube is integrally connected with the dropper connector and it is impossible to serially connect other infusion tubes therewith so that the infusion distance cannot be elongated.)

Figure 6:
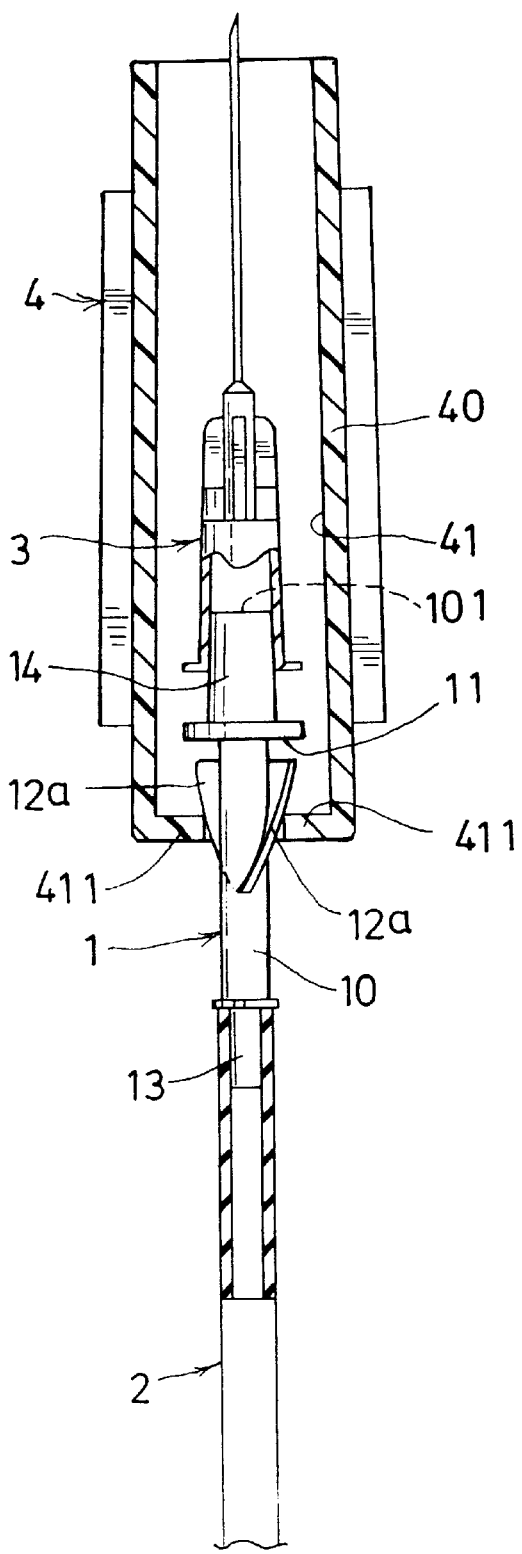
FIG. 6 shows another embodiment of the connecting tube of the present invention.

FIG. 6 shows a modification of the connecting tube 1, in which the guiding ribs 12a are spiralled around the tube body 10 of the connecting tube 1 so as to reduce the slope. Accordingly, when the latching flange 411 of the bottom end of the slide sleeve 4 is slided over the guiding ribs 12a, the latching flange 411 is more smoothly spirally guided to be latched in the latching groove 11 of the connecting tube 1. Therefore, the safety slide sleeve 4 can be operated more easily.

The multifunctional syringe of the present invention is characterized in that at least one guiding rib 12 axially downward extends from a lower side of the latching groove 11 of the connecting tube 1. The guiding rib 12 is downward tapered. When the latching flange 411 of the slide sleeve 4 is slided over the guiding rib 12, the bottom end of the slide sleeve 4 is slightly resiliently expanded, whereby the latching flange 411 can be smoothly latched in the latching groove 11 of the connecting tube 1 so as to totally enclose the injection needle 3. The present invention has advantages as follows:

1. The safety slide sleeve can be smoothly operated with little strength.
2. The syringe of the present invention has simple structure and can be easily operated.
3. The injection needle is hidden in the slide sleeve without exposure so as to avoid impalement of other people.
4. Multiple infusion tubes can be serially connected according to the requirement of actual medical site so as to elongate the infusion distance.

It is to be understood that the above description and drawings are only used for illustrating some embodiments of the present invention, not intended to limit the scope thereof. Any variation and derivation from the above description and drawings should be included in the scope of the present invention.

What is claimed is:

1. A multifunctional syringe with safety slide sleeve, comprising:

a connecting tube including a tube body formed with a central axial through hole, an infusion tube connecting section being formed at a bottom end of the tube body, a needle connecting section being formed at a top end of the tube body, a latching groove being formed on the tube body near the top end thereof, at least one downward tapered guiding rib being formed on the tube body and axially downward extending from a lower side of the latching groove;

an infusion tube serially connected with the infusion tube connecting section of the bottom end of the connecting tube;

an injection needle serially connected with the needle connecting section of the top end of the connecting tube; and a safety slide sleeve including a sleeve section formed with a central axial fitting hole in which the connecting tube is fitted, a bottom end of the fitting hole being formed with an inward extending latching flange, whereby when the slide sleeve is slided upward, the latching flange is guided by and slided over the guiding rib to be latched in the latching groove of the connecting tube so as to totally enclose the injection needle in the fitting hole.

2. A multifunctional syringe as claimed in claim 1, wherein an end of the infusion tube is connected with a connector for serially connecting with other infusion tubes.

3. A multifunctional syringe as claimed in claim 2, wherein a throttle is installed on the infusion tube and an input end of the infusion tube is serially connected with a connector.

4. A multifunctional syringe as claimed in claim 1, wherein said downward tapered guiding rib outward projects from the lower side of the latching groove and is downward tapered and spiraled around the tube body of the connecting tube.

5. A multifunctional syringe as claimed in claim 1, wherein multiple slip-proof ribs are axially formed on an outer circumference of the sleeve section of the slide sleeve.

* * * * *